US011376212B2

(12) United States Patent
Myoung et al.

(10) Patent No.: US 11,376,212 B2
(45) Date of Patent: Jul. 5, 2022

(54) **SKIN WHITENING COMPOSITION COMPRISING CULTURED PRODUCT OF *BACILLUS HWAJINPOENSIS* OR EXTRACT THEREOF**

(71) Applicant: Amorepacific Corporation, Seoul (KR)

(72) Inventors: Kilsun Myoung, Yongin-si (KR); Jaeyoung Ko, Yongin-si (KR); Yong Jin Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 16/647,135

(22) PCT Filed: Sep. 14, 2018

(86) PCT No.: PCT/KR2018/010855
§ 371 (c)(1),
(2) Date: Mar. 13, 2020

(87) PCT Pub. No.: WO2019/054800
PCT Pub. Date: Mar. 21, 2019

(65) Prior Publication Data
US 2021/0022988 A1 Jan. 28, 2021

(30) Foreign Application Priority Data
Sep. 15, 2017 (KR) ........................ 10-2017-0118928

(51) Int. Cl.
*A61K 8/99* (2017.01)
*A61Q 19/02* (2006.01)

(52) U.S. Cl.
CPC ................ *A61K 8/99* (2013.01); *A61Q 19/02* (2013.01)

(58) Field of Classification Search
CPC ........................................................ A61K 8/99
See application file for complete search history.

(56) References Cited

FOREIGN PATENT DOCUMENTS

| | | | | |
|---|---|---|---|---|
| JP | 2011-529484 A | | 12/2011 | |
| KR | 10-0812922 B1 | | 3/2008 | |
| KR | 10-2012-0068367 A | | 6/2012 | |
| KR | 10-2014-0073228 A | | 6/2014 | |
| KR | 10-2014-0097621 A | | 8/2014 | |
| KR | 10-1477886 B1 | | 1/2015 | |
| KR | 10-2015-0035659 A | | 4/2015 | |
| KR | 10-1583600 A | | 1/2016 | |
| KR | 10-2016-0132116 A | | 11/2016 | |
| KR | 20160034232 A | * | 2/2017 | ........... A61K 31/045 |
| KR | 10-1760766 B1 | | 7/2017 | |
| WO | WO2006117019 A1 | * | 9/2006 | ............. A61K 35/74 |
| WO | 2006/117019 A1 | | 11/2006 | |
| WO | 2010/013179 A1 | | 2/2010 | |
| WO | 2015/151009 A1 | | 10/2015 | |

OTHER PUBLICATIONS

Jung-Hoon Yoon, *Bacillus hwajinpoensis* sp. nov. and an unnamed *Bacillus* genomospecies, novel members of Bacillus rRNA group 6 isolated from sea water of the East Sea and the Yellow Sea in Korea, International Journal of Systematic and Evolutionary Microbiology (2004), 54, 803-808 (Year: 2004).*
KR20160034232A, Google English Translation, downloaded in Mar. 2021 (Year: 2021).*
Giorgio Lampis, Sattabacins and Sattazolins: New Biologically Active Compounds with Antiviral Properties Extracted from a *Bacillus* sp., Journal of Antibiotics vol. 48 No. 9, publication date: Sep. 1995 (Year: 1995).*
Bacillus hwajinpoensis strain CSR_18 16S ribosomal RNAgene, partial sequence, GenBank: KX035025.1, publication date: Jul. 13, 2016 (Year: 2016).*
"Bacillus hwajinpoensis strain CSR_18 16S ribosomal RNA gene, partial sequence", GenBank KX035025.1, Jul. 13, 2016, 2 pages.
Jung-Hoon Yoon et al., "*Bacillus hwajinpoensis* sp. nov. and an unnamed *Bacillus* genomospecies, novel members of Bacillus rRNA group 6 isolated from sea water of the East Sea and the Yellow Sea in Korea", International Journal of Systematic and Evolutionary Microbiology, 2004, pp. 803-808, vol. 54.
International Search Report for PCT/KR2018/010855, dated Jan. 2, 2019.
Communication dated Sep. 28, 2021 in Korean Application No. 10-2017-0118928.
Grant of Patent dated Mar. 30, 2022 from the Korean Intellectual Property Office in KR Application No. 10-2017-0118928.

* cited by examiner

*Primary Examiner* — Mark V Stevens
*Assistant Examiner* — Alparslan Asan
(74) *Attorney, Agent, or Firm* — Sughrue Mion, PLLC

(57) ABSTRACT

Disclosed in the present specification is a skin whitening composition comprising a *Bacillus hwajinpoensis* strain, a lysate thereof, a cultured product thereof or an extract of the strain, lysate or cultured product as an active ingredient. Disclosed in the present specification is a *Bacillus hwajinpoensis* strain SNC 135, having an accession number of KCCM12051P, which has a skin whitening function.

6 Claims, 2 Drawing Sheets

Specification includes a Sequence Listing.

【FIG. 1】

ATGCAAGTCGAGCGAAGAGATGGGAGCTTGCTCCCTGATCTTAGCGGCGGACGGGTGAGT
AACACGTGGGCAACCTGCCCTGCAGACTGGGATAACTCCGGGAAACCGGAGCTAATACCG
GGTAATACATCGCACCGCATGGTGCAATGTTGAAAGTTGGCTCTCTGAGCTAACACTGCA
GGATGGGCCCGCGGCGCATTAGCTAGTTGGTAAGGTAATGGCTTACCAAGGCGACGATGC
GTAGCCGACCTGAGAGGGTGATCGGCCACACTGGGACTGAGACACGGCCCAGACTCCTAC
GGGAGGCAGCAGTAGGGAATCTTCCGCAATGGACGAAAGTCTGACGGAGCAACGCCGCGT
GAGTGACGAAGGCCTTCGGGTCGTAAAGCTCTGTTGTTAGGGAAGAACAAGTACCGTTCG
AATAGGGCGGTACCTTGACGGTACCTAACCAGAAAGCCACGGCTAACTACGTGCCAGCAG
CCGCGGTAATACGTAGGTGGCAAGCGTTGTCCGGAATTATTGGGCGTAAAGCGCGCGCAG
GCGGTCTTTTAAGTCTGATGTGAAAGCCCACGGCTCAACCGTGGAGGGTCATTGGAAACT
GGAGGACTTGAGTGCAGAAGAGGAGAGTGGAATTCCACGTGTAGCGGTGAAATGCGTAGA
TATGTGGAGGAACACCAGTGGCGAAGGCGGCTCTCTGGTCTGTAACTGACGCTGAGGCGC
GAAAGCGTGGGGAGCAAACAGGATTAGATACCCTGGTAGTCCACGCCGTAAACGATGAGT
GCTAGGTGTTGGGGGGTTCCACCCTCAGTGCTGAAGTTAACACATTAAGCACTCCGCCTG
GGGAGTACGACCGCAAGGTTGAAACTCAAAGGAATTGACGGGGGCCCGCACAAGCAGTGG
AGCATGTGGTTTAATTCGAAGCAACGCGAAGAACCTTACCAGGTCTTGACATCCTCTGAC
AATCCTGGAGACAGGACGTTCCCCTTCGGGGGACAGAGTGACAGGTGGTGCATGGTTGTC
GTCAGCTCGTGTCGTGAGATGTTGGGTTAAGTCCCGCAACGAGCGCAACCCTTGATCTTA
GTTGCCAGCATTCAGTTGGGCACTCTAAGGTGACTGCCGGTGACAAACCGGAGGAAGGTG
GGGATGACGTCAAATCATCATGCCCCTTATGACCTGGGCTACACACGTGCTACAATGGAC
GGTACAAAGGGCAGCAACACCGCGAGGTGAAGCAAATCCCATAAAGCCGTTCTCAGTTCG
GATTGCAGGCTGCAACTCGCCTGCATGAAGCCGGAATTGCTAGTAATCGCGGATCAGCAT
GCCGCGGTGAATACGTTCCCGGGCCTTGTACACACCGCCCGTCACACCACGAGAGTTTGT
AACACCCGAAGTCGGTGGGGTAACCTTTATGGAGCCAGCCGC

【FIG. 2】
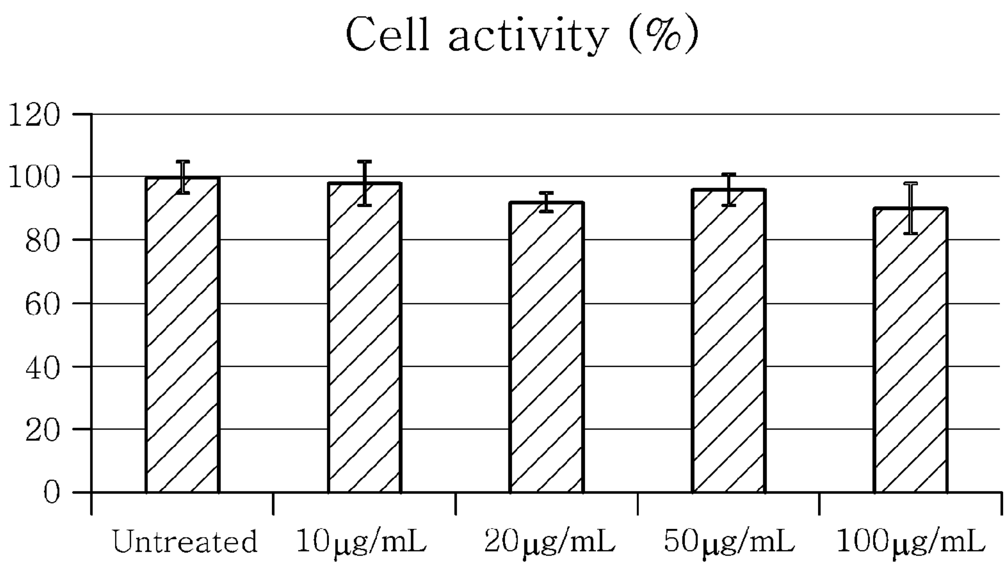
【FIG. 3】
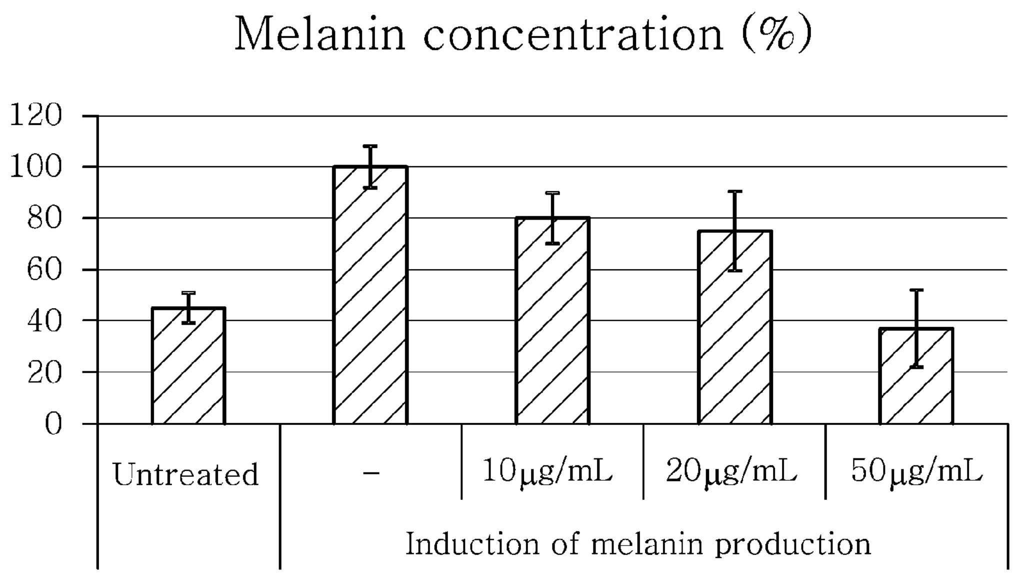

SEQUENCE LISTING

```
<160> NUMBER OF SEQ ID NOS: 3

<210> SEQ ID NO 1
<211> LENGTH: 1422
<212> TYPE: DNA
<213> ORGANISM: Unknown
<220> FEATURE:
<223> OTHER INFORMATION: Bacillus hwajinpoensis SNC 135

<400> SEQUENCE: 1

atgcaagtcg agcgaagaga tgggagcttg ctccctgatc ttagcggcgg acgggtgagt     60

aacacgtggg caacctgccc tgcagactgg gataactccg ggaaaccgga gctaataccg    120

ggtaatacat cgcaccgcat ggtgcaatgt tgaaagttgg ctctctgagc taacactgca    180

ggatgggccc gcggcgcatt agctagttgg taaggtaatg gcttaccaag gcgacgatgc    240

gtagccgacc tgagagggtg atcggccaca ctgggactga gacacggccc agactcctac    300

gggaggcagc agtagggaat cttccgcaat ggacgaaagt ctgacggagc aacgccgcgt    360
```

```
gagtgacgaa ggccttcggg tcgtaaagct ctgttgttag ggaagaacaa gtaccgttcg      420

aatagggcgg taccttgacg gtacctaacc agaaagccac ggctaactac gtgccagcag      480

ccgcggtaat acgtaggtgg caagcgttgt ccggaattat tgggcgtaaa gcgcgcgcag      540

gcggtctttt aagtctgatg tgaaagccca cggctcaacc gtggagggtc attggaaact      600

ggaggacttg agtgcagaag aggagagtgg aattccacgt gtagcggtga aatgcgtaga      660

tatgtggagg aacaccagtg gcgaaggcgg ctctctggtc tgtaactgac gctgaggcgc      720

gaaagcgtgg ggagcaaaca ggattagata ccctggtagt ccacgccgta aacgatgagt      780

gctaggtgtt gggggttcc accctcagtg ctgaagttaa cacattaagc actccgcctg       840

gggagtacga ccgcaaggtt gaaactcaaa ggaattgacg ggggcccgca caagcagtgg      900

agcatgtggt ttaattcgaa gcaacgcgaa gaaccttacc aggtcttgac atcctctgac      960

aatcctggag acaggacgtt ccccttcggg ggacagagtg acaggtggtg catggttgtc     1020

gtcagctcgt gtcgtgagat gttgggttaa gtcccgcaac gagcgcaacc cttgatctta     1080

gttgccagca ttcagttggg cactctaagg tgactgccgg tgacaaaccg gaggaaggtg     1140

gggatgacgt caaatcatca tgccccttat gacctgggct acacacgtgc tacaatggac     1200

ggtacaaagg gcagcaacac cgcgaggtga agcaaatccc ataaagccgt tctcagttcg     1260

gattgcaggc tgcaactcgc ctgcatgaag ccggaattgc tagtaatcgc ggatcagcat     1320

gccgcggtga atacgttccc gggccttgta cacaccgccc gtcacaccac gagagtttgt     1380

aacacccgaa gtcggtgggg taacctttat ggagccagcc gc                        1422

<210> SEQ ID NO 2
<211> LENGTH: 20
<212> TYPE: DNA
<213> ORGANISM: Artificial Sequence
<220> FEATURE:
<223> OTHER INFORMATION: 27F primer

<400> SEQUENCE: 2

agagtttgat cmtggctcag                                                    20

<210> SEQ ID NO 3
<211> LENGTH: 22
<212> TYPE: DNA
<213> ORGANISM: Artificial Sequence
<220> FEATURE:
<223> OTHER INFORMATION: 1492R primer

<400> SEQUENCE: 3

tacggytacc ttgttacgac tt                                                 22
```

SKIN WHITENING COMPOSITION COMPRISING CULTURED PRODUCT OF *BACILLUS HWAJINPOENSIS* OR EXTRACT THEREOF

CROSS REFERENCE TO RELATED APPLICATIONS

This application is a National Stage of International Application No. PCT/KR2018/010855 filed Sep. 14, 2018, claiming priority based on Korean Patent Application No. 10-2017-0118928 filed Sep. 15, 2017.

TECHNICAL FIELD

Disclosed in the present specification is a skin whitening composition containing a *Bacillus hwajinpoensis* strain, a lysate thereof, a cultured product thereof, or an extract of the strain, lysate or cultured product as an active ingredient.

BACKGROUND ART

Human skin color is determined by carotene, the amount of melanin, hemoglobin, etc. Among them, melanin plays the most important role. Melanin is a pigment responsible for skin color and the color of hair and eye and plays an important role of protecting human skin. However, excessive production of melanin in the skin due to external environments such as excessive exposure to UV, air pollution, stress, etc. causes skin darkening, liver spots, freckles, etc. UV radiation is the major factor that induces melanin overproduction through promotion of the activity of melanin-producing melanocytes, promotion of the secretion of melanin biosynthesis-stimulating hormones, promotion of melanin oxidation, promotion of tyrosinase activity, etc.

A *Bacillus hwajinpoensis* strain is one of marine bacteria. The strain was discovered in 2004 by the researchers of the Korea Research Institute of Bioscience and Biotechnology, but nothing is known about its use.

REFERENCES OF RELATED ART

Patent Documents

Korean Patent Registration Publication No. 10-0812922.

DISCLOSURE

Technical Problem

In an aspect, the present specification is directed to providing a new use of a *Bacillus hwajinpoensis* strain.

In another aspect, the present specification is directed to providing a *Bacillus hwajinpoensis* SNC 135 strain having superior skin whitening activity.

Technical Solution

In another aspect, the present specification provides a skin whitening composition containing: a *Bacillus hwajinpoensis* strain; a lysate thereof; a cultured product thereof; or an extract of the strain, lysate or cultured product as an active ingredient.

In an exemplary embodiment, the strain may be *Bacillus hwajinpoensis* SNC 135 having an accession number of KCCM12051P.

In an exemplary embodiment, the strain may have 16S rDNA including a base sequence of SEQ ID NO 1.

In an exemplary embodiment, the cultured product may be cultured in a culture medium including one or more selected from a group consisting of starch, yeast extract, peptone and sea salt.

In an exemplary embodiment, the extract may be an ethyl acetate fraction.

In an exemplary embodiment, the active ingredient may be contained in an amount of 0.001-30 wt % based on the total weight of the composition.

In an exemplary embodiment, the composition may inhibit melanin production or tyrosinase activity.

In an exemplary embodiment, the composition may be a cosmetic composition.

In another aspect, the present specification provides a *Bacillus hwajinpoensis* SNC 135 strain having an accession number of KCCM12051P, having skin whitening function.

In an exemplary embodiment, the strain may be isolated from coral.

Advantageous Effects

In an aspect, the present specification provides an environment-friendly skin whitening ingredient.

In another aspect, the present specification provides a use of a *Bacillus hwajinpoensis* strain for skin whitening. The strain has an effect of inhibiting melanin production in melanocytes.

In another aspect, the present specification provides a *Bacillus hwajinpoensis* SNC 135 strain having superior skin whitening activity.

BRIEF DESCRIPTION OF DRAWINGS

FIG. 1 shows the 16s rDNA sequence (SEQ ID NO 1) of a *Bacillus hwajinpoensis* SNC 135 strain having an accession number of KCCM12051P according to the present specification.

FIG. 2 shows the skin cell safety of a *Bacillus hwajinpoensis* strain according to an exemplary embodiment of the present specification.

FIG. 3 shows the melanin production inhibiting effect of a *Bacillus hwajinpoensis* strain according to an exemplary embodiment of the present specification.

BEST MODE

Hereinafter, the present disclosure is described in detail.

In an aspect, the present specification provides a skin whitening composition containing: a *Bacillus hwajinpoensis* strain; a lysate thereof; a cultured product thereof; or an extract of the strain, lysate or cultured product as an active ingredient.

In another aspect, the present specification provides a method for enhancing skin whitening, which includes administering a *Bacillus hwajinpoensis* strain, a lysate thereof, a cultured product thereof, or an extract of the strain, lysate or cultured product of an amount effective for enhancing skin whitening to a subject in need thereof.

In another aspect, the present specification provides a *Bacillus hwajinpoensis* strain, a lysate thereof, a cultured product thereof, or an extract of the strain, lysate or cultured product for enhancing skin whitening of a subject.

In another aspect, the present specification provides a non-therapeutic use of a *Bacillus hwajinpoensis* strain, a lysate thereof, a cultured product thereof, or an extract of the strain, lysate or cultured product for enhancing skin whitening of a subject.

In another aspect, the present specification provides a use of a *Bacillus hwajinpoensis* strain, a lysate thereof, a cultured product thereof, or an extract of the strain, lysate or cultured product for preparing a composition for enhancing skin whitening.

In another aspect, the present specification provides a *Bacillus hwajinpoensis* SNC 135 strain having an accession number of KCCM12051P.

In an exemplary embodiment, the *Bacillus hwajinpoensis* strain, the lysate thereof, the cultured product thereof, or the extract of the strain, lysate or cultured product may be administered or applied or spreaded to a subject in the form of a composition, e.g., a composition for external application to skin or a cosmetic composition.

In an exemplary embodiment, the *Bacillus hwajinpoensis* strain, the lysate thereof, the cultured product thereof, or the extract of the strain, lysate or cultured product may be administered to the skin of a subject.

In an exemplary embodiment, the strain may be preferred to be *Bacillus hwajinpoensis* SNC 135 having an accession number of KCCM12051P.

In an exemplary embodiment, the strain may have 16S rDNA including the base sequence of SEQ ID NO 1.

In an exemplary embodiment, the *Bacillus hwajinpoensis* SNC 135 strain may have skin whitening function.

In the present specification, the "active ingredient" refers to an ingredient capable of affording a desired activity either alone or together with a carrier, etc. which has no activity in itself.

Microbial resources are advantageous in that they can be utilized as renewable resources unlike petroleum, water, etc.

In an exemplary embodiment, the strain may be prepared as follows. After culturing the strain and centrifuging the culture medium, followed by washing with sterilized physiological saline and suspending in a solvent, e.g., sterilized milk, it may be prepared into freeze-dried powder.

The lysate of the strain may refer to a product obtained by lysing the strain itself either chemically or by applying physical force.

The cultured product of the strain may refer to a material comprising some or all substances included in the culture medium in which the strain was cultured, regardless of the type of the cultured product. For example, it may refer to a material including a metabolite or a secreted product resulting from the culturing of the strain, or a lysate thereof, and the strain itself may also be included in the cultured product.

In an exemplary embodiment, the cultured product may be cultured in a culture medium including one or more selected from a group consisting of starch, yeast extract, peptone and sea salt.

The extract may refer to a product obtained by extracting, isolating or fractionating the strain itself, a lysate of the strain, a cultured product of the strain or a mixture thereof, regardless of extraction method, extraction solvent, extracted ingredients or type of the extract. The term is used in a broad concept, including any substance that can be obtained through processing or treating after the extraction.

In an exemplary embodiment, the extract may be preferred to be an ethyl acetate fraction of a culture of *Bacillus hwajinpoensis*.

In an exemplary embodiment, the *Bacillus hwajinpoensis* strain, the lysate thereof, the cultured product thereof, or the extract of the strain, lysate or cultured product may be contained in an amount of 0.001-30 wt % based on the total weight of the composition. In another aspect, the *Bacillus hwajinpoensis* strain, the lysate thereof, the cultured product thereof, or the extract of the strain, lysate or cultured product may be contained in an amount of 0.001 wt % or more, 0.01 wt % or more, 0.1 wt % or more, 0.5 wt % or more, 1 wt % or more, 1.5 wt % or more or 2 wt % or more, and 30 wt % or less, 25 wt % or less, 20 wt % or less, 15 wt % or less, 10 wt % or less or 5 wt % or less, based on the total weight of the composition.

The *Bacillus hwajinpoensis* strain, the lysate thereof, the cultured product thereof, the extract of the strain, lysate or cultured product, or the skin whitening composition containing the same according to the present disclosure has an effect of preventing, improving and/or treating a symptom or a disease caused by melanin overproduction by effectively inhibiting melanin production.

In an exemplary embodiment, the symptom or disease caused by melanin overproduction may be one or more selected from a group consisting of liver spots, freckles, age spots, blemish, epidermal melanocytic lesions, café au lait macules, Beckers nevus, nevus spilus, lentigines, dermal melanocytic lesions, Mongolian spot, nevus of Ota, acquired bilateral nevus of Ota-like macules, nevus of Ito, blue nevus, melanocytic nevus, junctional nevus, compound nevus, intradermal nevus, halo nevus, congenital nevocytic nevus, Spitz nevus, dysplastic nevus, melanoma, lentigo maligna melanoma, superficial spreading melanoma, acral lentiginous melanoma, nodular melanoma, pigmented basal cell carcinoma, pigmented dermatofibromas, dermoid cyst, pigmented keloid and pigmented keratoacanthomas.

In an exemplary embodiment, the *Bacillus hwajinpoensis* strain, the lysate thereof, the cultured product thereof, the extract of the strain, lysate or cultured product, or the composition containing the same may prevent, improve and/or treat skin pigmentation.

In an exemplary embodiment, the *Bacillus hwajinpoensis* strain, the lysate thereof, the cultured product thereof, the extract of the strain, lysate or cultured product, or the composition containing the same may prevent, improve and/or treat one or more skin pigmentation selected from a group consisting of liver spots, freckles, dark spots, nevus, melanoma, drug-induced pigmentation, inflammation-induced pigmentation and dermatitis-induced pigmentation, which occurs topically in skin due to increased melanin production.

In an exemplary embodiment, the composition may be a composition for external application to skin.

In an exemplary embodiment, the composition for external application to skin may further contain a pharmaceutical adjuvant such as antiseptic, a stabilizer, a wetting agent, an emulsification promoter, a salt and/or a buffer for controlling osmotic pressure, etc. and other therapeutically useful substances in addition to the active ingredient according to the present specification, and may be formulated into various forms for parenteral application according to common methods.

In an exemplary embodiment, the formulation for parenteral application may be for transdermal application. For example, the formulation may be an injection, an ointment, a lotion, a gel, a cream, a spray, a suspension, an emulsion, a patch, etc., although not being limited thereto.

In an exemplary embodiment, the composition for external application to skin may be a topical medication having pharmaceutical use for a disease related with melanin production.

In an exemplary embodiment, the composition may be a cosmetic composition.

In an exemplary embodiment, the cosmetic composition may further contain functional additives and ingredients contained in general cosmetic compositions in addition to the active ingredient according to the present specification. The functional additive may be an ingredient selected from a group consisting of a water-soluble vitamin, an oil-soluble vitamin, a polypeptide, a polysaccharide, a sphingolipid and a seaweed extract. In addition, an ingredient such as an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a fragrance, a blood circulation stimulant, a cooling agent, an antiperspirant, purified water, etc. may be further contained.

The formulation of the cosmetic composition is not particularly limited and may be selected adequately depending on purposes. For example, the cosmetic composition may be prepared into one or more formulation selected from a group consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

In an exemplary embodiment, when the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

In an exemplary embodiment, when the formulation of the present disclosure is a powder or a spray, lactose, talc, silica, aluminum hydroxide, calcium silicate or polyamide powder may be used as a carrier ingredient. In particular, when the formulation is a spray, it may further contain a propellant such as chlorofluorohydrocarbon, propane/butane or dimethyl ether.

In an exemplary embodiment, when the formulation of the present disclosure is a solution or an emulsion, a solvent, a solubilizer or an emulsifier, e.g., water, ethanol, isopropanol, ethyl carbonate, ethyl acetate, benzyl alcohol, benzyl benzoate, propylene glycol, 1,3-butylene glycol, a glycerol aliphatic ester, polyethylene glycol or a fatty acid ester of sorbitan may be used as a carrier ingredient.

In an exemplary embodiment, when the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

In an exemplary embodiment, when the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an amidoalkyl betaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

Mode for Invention

Hereinafter, the present disclosure will be described in detail through examples. However, the following examples are for illustrative purposes only and it will be apparent to those of ordinary skill in the art that the scope of the present disclosure is not limited by the examples.

Example 1. Isolation and Identification of Strain

Harvested coral (scleractinia) was heat-treated at 60° C. for 10 minutes to remove Gram-negative bacteria on the coral surface. Then, microorganisms existing on the coral surface were isolated using physiological saline (0.85% NaCl). The physiological saline solution was diluted 10-fold and 100-fold using physiological saline and then inoculated to an isolation medium (10 g/L starch, 4 g/L yeast extract, 2 g/L peptone, 16 g/L agar, 34.75 g/L sea salt) supplemented with an antibiotic (chloramphenicol 20 μg/mL). The inoculated medium was incubated at 27° C. for 7-30 days, and a single strain forming a colony was isolated finally by subculturing for 2-4 passages.

The isolated strain was identified through 16S rRNA base sequencing using 27F (5'-AGAGTTTGATCMTGGCTCAG-3', SEQ ID NO 2) and 1492R (5'-TACGGYTACCTTGTTACGACTT-3', SEQ ID NO 3) primers. As a result of Gene Bank search, the isolated strain was confirmed to have 99.4% similarity to *Bacillus hwajinpoensis* strain SW-72 and named as *Bacillus hwajinpoensis* SNC 135. The strain was deposited on Jun. 27, 2017 in the Korean Culture Center of Microorganisms (KCCM) and was given the accession number KCCM12051P.

Example 2. Preparation of Cultured Product and Extract of *Bacillus hwajinpoensis* Strain The *Bacillus hwajinpoensis* SNC 135 strain identified in Example 1 was inoculated to a culture medium (10 g/L starch, 2 g/L yeast extract, 4 g/L peptone, 34.75 g/L sea salt) and a culture of the *Bacillus hwajinpoensis* strain was obtained by culturing the same at 27° C. and 120 rpm for 7 days.

The obtained culture of the *Bacillus hwajinpoensis* strain was added to ethyl acetate of the same volume and an ethyl acetate fraction was obtained by conducting reaction. Then, an extract was obtained by removing the ethyl acetate using an evaporator.

Example 3. Confirmation of Skin Cell Safety of *Bacillus hwajinpoensis* Strain Experiment was conducted as follows to investigate whether the *Bacillus hwajinpoensis* strain is safe for skin cells.

Specifically, after dissolving the extract of the *Bacillus hwajinpoensis* strain isolated from the coral obtained in Example 2 in DMSO (dimethyl sulfoxide) and treating skin cells (HaCaT) with the extract, the effect on the activity of the cells was investigated. After seeding 100 μL of the skin cells onto a 96-well cell culture plate at a concentration of $2\times10^5$ cells/mL and culturing for 24 hours, followed by treating with the extract of the *Bacillus hwajinpoensis* strain at concentrations of 10-100 μg/mL, the cells were cultured further for 24 hours. The experiment was repeated 3 times for the respective concentrations. The cell activity was compared by MTT assay and was represented relative to the activity of the untreated group as 100%.

As a result, the *Bacillus hwajinpoensis* strain isolated from the coral was confirmed to be safe the skin cells since they had no effect on the growth of the skin cells (see FIG. 2).

Example 4. Confirmation of Skin Whitening Effect of *Bacillus hwajinpoensis* Strain The skin whitening effect of the *Bacillus hwajinpoensis* strain was tested as follows.

Specifically, the skin whitening effect was evaluated by treating melanocytes (B16 melanoma cells) with the extract of the *Bacillus hwajinpoensis* strain isolated from the coral obtained in Example 2. The melanocytes seeded onto a 24-well cell culture plate at a concentration of $4\times10^4$ cells/well and cultured for 24 hours were used for the experiment. The cells were treated with 1 μM α-MS H (α-melanocyte-stimulating hormone) to induce melanin production and at the same time with the extract of the *Bacillus hwajinpoensis* strain at concentrations of 10-50 μg/mL. The experiment was repeated 3 times for the respective concentrations. After culturing further for 72 hours, absorbance was measured at 405 nm in order to compare the melanin content in the culture medium. The degree of melanin production of the groups treated with the extract was represented relative to the absorbance of the melanin production-induced group as 100%.

As a result, it was confirmed that the extract inhibited the melanin production in the melanocytes in a concentration-dependent manner, suggesting that the *Bacillus hwajinpoensis* strain has skin whitening effect (see FIG. 3).

Hereinafter, formulation examples of the composition according to an aspect of the present disclosure will be described. However, the following formulation examples are for illustrative purposes only and the scope of the present disclosure is not limited by them.

Formulation Example 1. Softening Lotion

A softening lotion was prepared according to a common method by mixing 0.01 wt % of the *Bacillus hwajinpoensis* culture of Example 2, 3 wt % of glycerin, 2 wt % of butylene glycol, 2 wt % of propylene glycol, 0.1 wt % of a carboxyvinyl polymer, 10 wt % of ethanol, 0.1 wt % of triethanolamine, an antiseptic as balance, a trace amount of a colorant, a trace amount of a fragrance and a trace amount of purified water.

Formulation Example 2. Nourishing Lotion

A nourishing lotion was prepared according to a common method by mixing 0.01 wt % of the *Bacillus hwajinpoensis* culture of Example 2, 4 wt % of beeswax, 1.5 wt % of polysorbate 60, 0.5 wt % of sorbitan sesquioleate, 5 wt % of liquid paraffin, 5 wt % of squalane, 5 wt % of caprylic/capric triglyceride, 3 wt % of glycerin, 3 wt % of butylene glycol, 3 wt % of propylene glycol, 0.1 wt % of a carboxyvinyl polymer, 0.2 wt % of triethanolamine, an antiseptic as balance, a trace amount of a colorant, a trace amount of a fragrance and a trace amount of purified water.

Formulation Example 3. Nourishing Cream

A nourishing cream was prepared according to a common method by mixing 0.01 wt % of the *Bacillus hwajinpoensis* culture of Example 2, 10 wt % of beeswax, 1.5 wt % of polysorbate 60, 0.5 wt % of sorbitan sesquioleate, 10 wt % of liquid paraffin, 5 wt % of squalane, 5 wt % of caprylic/capric triglyceride, 5 wt % of glycerin, 3 wt % of butylene glycol, 3 wt % of propylene glycol, 0.2 wt % of triethanolamine, an antiseptic as balance, a trace amount of a colorant, a trace amount of fragrance and a trace amount of purified water.

Formulation Example 4. Pack

A pack was prepared according to a common method by mixing 0.01 wt % of the *Bacillus hwajinpoensis* culture of Example 2, 13 wt % of polyvinyl alcohol, 0.2 wt % of sodium carboxymethyl cellulose, 0.1 wt % of allantoin, 5 wt % of ethanol, 0.3 wt % of nonyl phenyl ether, an antiseptic as balance, a trace amount of a colorant, a trace amount of fragrance and a trace amount of purified water.

Although the particular embodiments of the present disclosure have been described in detail, it will be apparent to those of ordinary skill in the art that they are only specific exemplary embodiments and the scope of the present disclosure is not limited by them. Accordingly, the substantial scope of the present disclosure will be defined by the appended claims and their equivalents.

[Accession Number]

Depository authority: Korean Culture Center of Microorganisms

Accession number: KCCM12051P

The invention claimed is:

1. A method for enhancing skin whitening of a subject in need thereof, which comprises administering an effective amount of an extract of a culture of a *Bacillus hwajinpoensis* strain to the subject,
   wherein the strain is *Bacillus hwajinpoensis* SNC 135 with accession number of KCCM12051P;
   wherein the extract is an ethyl acetate fraction; and
   wherein the extract is administered in form of a composition, and the extract is in an amount of 0.005-0.01 wt % based on the total weight of the composition.

2. The method according to claim 1, wherein the strain has 16S rDNA comprising the nucleotide sequence of SES ID NO: 1.

3. The method according to claim 1, wherein the culture of *Bacillus hwajinpoensis* strain is obtained by culturing *Bacillus hwajinpoensis* strain in a culture medium comprising one or more selected from the group consisting of starch, yeast extract, peptone, and sea salt.

4. The method according to claim 1, wherein the extract is in an amount of 0,005 wt % based on the total weight of the composition.

5. The method according to claim 4, wherein the composition inhibits melanin production.

6. The method according to claim 4, wherein the composition is a cosmetic composition.

* * * * *